United States Patent
Grundei

(10) Patent No.: US 6,869,450 B2
(45) Date of Patent: Mar. 22, 2005

(54) SUBCUTANEOUS, INTRAMUSCULAR SUPPORT FOR A RIGID TRANSCUTANEOUS IMPLANT

(75) Inventor: Hans Grundei, Lübeck (DE)

(73) Assignee: ESKA Implants GmbH & Co., Lübeck (DE)

(*) Notice: Subject to any disclaimer, the term of this patent is extended or adjusted under 35 U.S.C. 154(b) by 0 days.

(21) Appl. No.: 10/678,707

(22) Filed: Oct. 2, 2003

(65) Prior Publication Data

US 2004/0068324 A1 Apr. 8, 2004

(30) Foreign Application Priority Data

Oct. 8, 2002 (DE) .......................................... 102 47 397
Mar. 12, 2003 (DE) .......................................... 103 11 990

(51) Int. Cl.⁷ ................................................. A61F 2/60
(52) U.S. Cl. ....................................................... 623/32
(58) Field of Search ............................ 623/32, 27, 38, 623/53

(56) References Cited

U.S. PATENT DOCUMENTS

| | | | | | |
|---|---|---|---|---|---|
| 3,947,897 A | * | 4/1976 | Owens | ...................... | 623/11.11 |
| 4,143,426 A | * | 3/1979 | Hall et al. | ..................... | 623/53 |
| 4,158,895 A | * | 6/1979 | Frosch et al. | ................. | 606/60 |
| 5,002,578 A | * | 3/1991 | Luman | ..................... | 623/22.42 |
| 5,041,137 A | * | 8/1991 | Nemoshkalov | ............. | 128/898 |
| 5,759,206 A | * | 6/1998 | Bassett | ........................ | 623/27 |
| 6,425,925 B1 | * | 7/2002 | Grundei | ........................ | 623/32 |
| 6,482,238 B1 | * | 11/2002 | Grundei | ....................... | 623/32 |
| 6,485,522 B1 | * | 11/2002 | Grundei | ....................... | 623/38 |

FOREIGN PATENT DOCUMENTS

| | | |
|---|---|---|
| DE | 199 31 882 C | 5/2001 |
| DE | 100 40 590 A1 | 3/2002 |

\* cited by examiner

*Primary Examiner*—Alvin Stewart
(74) *Attorney, Agent, or Firm*—Akin Gump Strauss Hauer & Feld, LLP

(57) ABSTRACT

A subcutaneous, intramuscular support (1) is provided for a rigid transcutaneous implant (2), which can be anchored intracorporeally in a bone stump. The support has an intermediate piece (3) between the part of the implant (2) to be intracorporeally anchored and an extracorporeal coupling device (4) that can be coupled to it. A rigid bushing (5) is firmly connected with the intermediate piece (3), such that an annulus (6) is formed between the wall of the bushing (5) and the intermediate piece (3), the annulus being closed in the intracorporeal direction, and into which annulus the extracorporeal coupling device can be inserted. A tube (7) made of a flexible material is applied to the outer wall of the bushing (5), and a metallic wool (8) is applied to the flexible tube (7).

14 Claims, 3 Drawing Sheets

SUBCUTANEOUS, INTRAMUSCULAR SUPPORT FOR A RIGID TRANSCUTANEOUS IMPLANT

BACKGROUND OF THE INVENTION

This invention pertains to a subcutaneous, intramuscular support for a rigid transcutaneous implant, which can be anchored intracorporeally in a bone stump and which has an intermediate piece between the part to be intracorporeally anchored and an extracorporeal coupling device, which can be coupled to it.

Such a support is known from German published patent application DE 100 40 590 A1. The support described there is made of a flexible material and has a socket that firmly surrounds the implant distally, as well as an intracorporeally arranged cover sleeve in the form of a flexible bellows, that is connect proximally to the socket in a sealed manner by a collar formed on it, such that between the inner wall of the bellows and the outer wall of the socket, a hollow space with a minimum width remains free. Here, distally at the bellows, a flexible screen network is arranged, distal to which is another screen network with a higher modulus of elasticity.

This support has the goal to allow soft tissue to move relative to the rigid implant, without subjecting the point of penetration in the stump of the body to an increased risk of inflammation. Although this known support has already been successfully used in practice, the risk remains, for example when cleaning the point of penetration of the implant through the thigh stump using a cannula, that the flexible material, which in most cases is silicone, could be punctured, resulting in infection.

BRIEF SUMMARY OF THE INVENTION

Proceeding from this background, it is now an objective of the present invention to further develop a subcutaneous intramuscular support of the type mentioned above, such that safety is significantly increased against an infection of the implant penetration and of the adjacent areas of the thigh stump, and such that any accidental breaching of the germ barrier is prevented.

This objective is achieved according to the invention for a subcutaneous, intramuscular support for a rigid transcutaneous implant, which is intracorporeally anchorable in a bone stump and which has an intermediate piece between the part to be intracorporeally anchored and an extracorporeal coupling device couplable thereto, wherein it is proposed: that the support have a rigid bushing that is firmly connected to the intermediate piece, in such a way that an annulus is formed between the wall of the bushing and the intermediate piece, the annulus being closed in the intracorporeal direction, and the extracorporeal coupling device being insertable into this annulus; that the support bushing have a tube made of flexible material applied to the outer wall of the bushing; and that a metallic wool be applied to the flexible tube. Advantageous improvements are describe below and in the dependent claims.

In comparison to the known support, the bushing here is a rigid element that cannot by chance be punctured by injection cannulas. The tube made of flexible material, preferably silicone, attached to the outer wall of the bushing, effects an equalization between the tissue and the muscles, on the one hand, and the rigid connection to the bone stump, on the other side. The metallic wool applied to the flexible tube serves for ingranulation of the surrounding tissue, which further increases the germ barrier.

The bushing can be firmly fastened to the intermediate piece by shrinking onto it. Alternatively, it can be welded to it. It is also possible to construct the bushing and the intermediate piece as one piece.

The metallic wool is preferably made of titanium fibers, which is a animal body-compatible metal. The intermediate piece is preferably constructed as a double cone with a cylindrical center section to which the bushing is connected.

Germs or contaminant particles cannot penetrate to the bone stump when using the support according to the invention, but are effectively blocked. An accidental injection of germs, for example, is not possible when using an injection needle, since the bushing is made of a rigid, preferably metallic material. An especially preferred material is titanium.

The germ barrier can be even further increased according to an especially preferred embodiment by attaching to the flexible tube a multi-layered metallic web and/or fabric and/or mesh and/or a multi-layered metallic wool, which extends around the intermediate piece in the form of a cap. In contrast to the basic support described above, in this case a multi-layered metallic web, fabric, mesh and/or a multi-layered metallic wool is thus used, into which tissue material can grow, thus offering an even further increase in the germ barrier. The distal end material of the flexible tube, which extends from the bushing in the form of a cap, is very much shorter than the screen network mentioned above. Here, the area taken up by the multi-layered metallic web, fabric, mesh and/or the multi-layered metallic wool is very much larger than in the support mentioned above.

The flexible tube and the distal, cap-shaped extension thereto aid in the isoelasticity and facilitate micro motions of the implant. The flexible tube is again preferred to be made of silicone.

So that the cap-shaped, multi-layered metallic web, fabric, mesh and/or the multi-layered metallic wool, extending around the intermediate piece, is easier to handle, i.e., easier to adapt to the anatomical features during the operation, an especially preferred embodiment provides that the multi-layered metallic web, fabric, mesh and/or the multi-layered metallic wool has radial lines, preferably at the periphery, along which the multiple layers are welded together. These welds are preferably produced using a laser. These lines allow a better adaptability to the anatomical features of the patient. It is also conceivable to envision these lines as cutting lines, along which the multi-layered metallic web, fabric, mesh and/or the multi-layered metallic wool can be cut to size, wherein the welds prevent fraying of the multi-layered metallic web, fabric, mesh and/or the multi-layered metallic wool from occurring.

In addition, another preferred embodiment provides at least two slotted, bent clamping rings that can be placed over the bushing, in such a way that during the operation they can be slid onto the bushing longitudinally with little play, and between their bent ends grasp at least one layer of a metallic web, fabric, mesh and/or attached metallic wool, which extends over the intermediate piece in the form of a cap.

This particularly preferred embodiment makes it possible for the implant to enter into a bond with the surrounding tissue which is as stress-free as possible. Thereby, since the at least two clamping rings with at least one layer in between them are mounted by longitudinal sliding onto the bushing, the position of this layer is adjusted according to the operating circumstances, and indeed is completely independent of the position of the flexible tube located on the outer wall of the bushing and the metallic wool attached to it. This embodiment gives the surgeon more degrees of freedom than the above-described embodiment in which the flexible tube transitions in the distal region into a cap-shaped enclosure of the intermediate piece. In the advantageous embodiment described here, the flexible tube on the bushing is constructed considerably shorter, in order to show the adjustment possibilities with regard to the position of the layer, in which binding tissue will be ingrained. What is significant here is thus the independence of the layer, for example made of metallic wool, that surrounds the intermediate piece, from the metallic wool connected to the silicone tube on the bushing. This in itself provides the position adjustability. It makes possible a substantially stress-free connection between the implant and the surrounding tissue, and thereby facilitates a lasting healing of the implant in the stump of the extremity.

This embodiment is also advantageously further improved in that the mentioned layers are arranged between any two adjacent clamping rings, in the case where there are more than two clamping rings. Depending on the spatial circumstances in situ, it may be indicated that more than two clamping rings, for example three or four clamping rings, need to be pushed onto the bushing, wherein one layer made of metallic wool, for example, is always arranged between two respective adjacent clamping rings. In this case, multiple metallic wool layers, for example, are inserted, thereby increasing the germ barrier even further.

The above embodiment can be even further improved by including a slotted, bent locking ring that engages the inner wall of the annulus with very little play and that locks the distal layer, made of metallic wool for example, against the next clamping ring. This locking ring is inserted when the surgeon has determined the optimum number of clamping rings and layers made of metallic wool for example, and then wishes to close the built up arrangement. After pressing the locking ring into the bushing, it is no longer possible to shift the arrangement longitudinally on the bushing.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

In the following, like parts are provided with the same reference numbers.

DETAILED DESCRIPTION OF THE INVENTION

Figure 1:
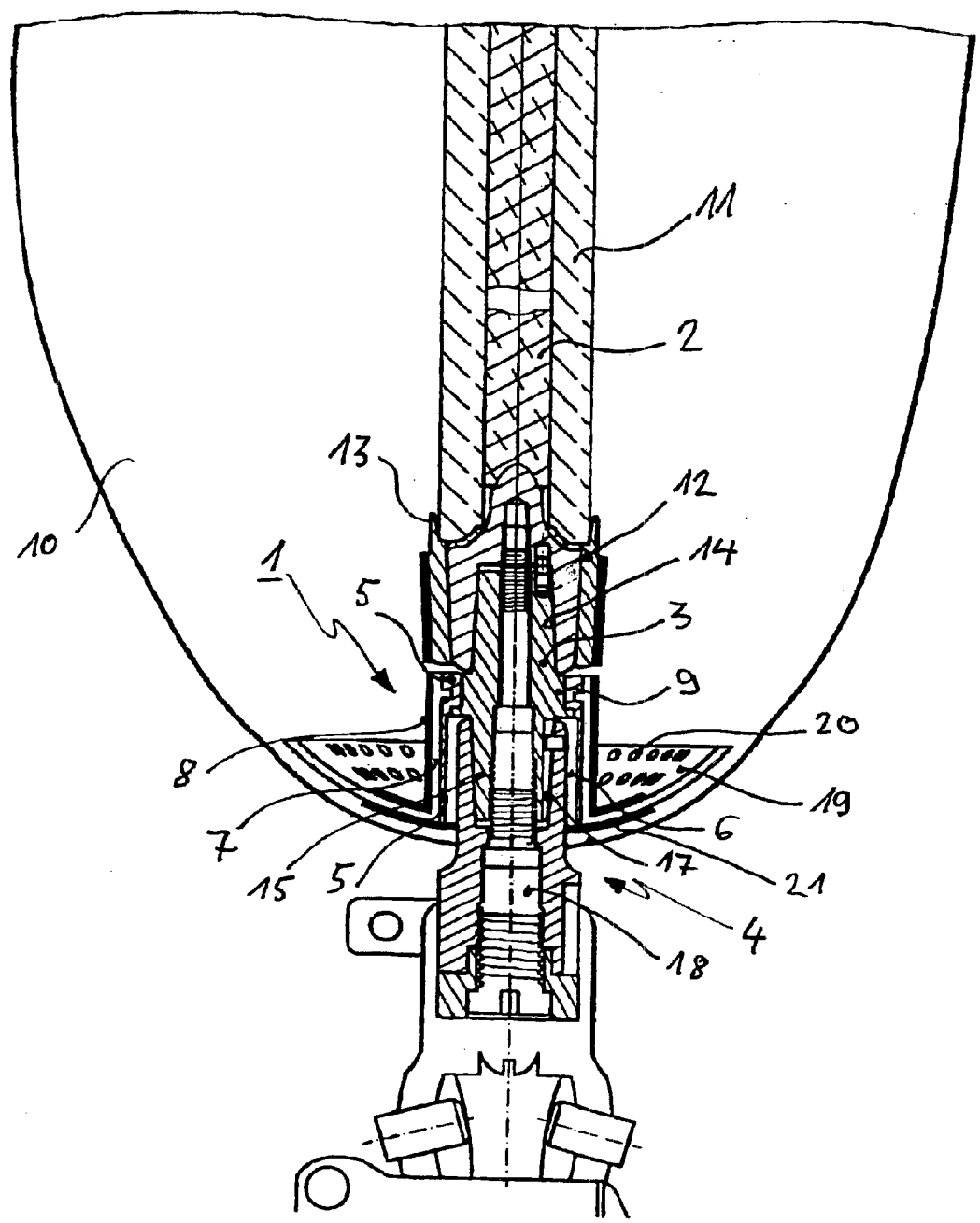
FIG. 1 is a schematic sectional view through a thigh stump and through the implanted subcutaneous support according to a first embodiment of the invention.

As shown in FIG. 1, the thigh stump is designated in general with the reference number 10. The bone stump 11 in this case is the stump of a femur. A rigid transcutaneous implant 2 is inserted in the femur stump 11. The implant is closed off distally by a metal sleeve 12, which has a proximal peripheral flange 13, which encloses the femur stump 11.

Inside the metal sleeve 12 is formed a conical clamping sleeve 14. This is provided to produce a conical clamp connection with the intermediate piece 3, which in this case is designed as a double cone. The intermediate piece 3 has a cylindrical center section 9 onto which the bushing 5 is shrunk in this case. Another cone 15 lies distally adjacent to the center section 9 to produce a conical clamp connection to a conical clamping sleeve 17 in an adapter of the extracorporeal coupling device 4.

The bushing 5 is designed such that an annulus 6 is formed between its wall and the intermediate piece, the annulus being closed in the intracorporeal or proximal direction. The extracorporeal coupling device 4 is inserted in this annulus 6. The connection between the subcutaneous support and the coupling device 4 is locked into place using a fastener 18.

A tube 7 made of silicone is attached to the outer wall of the bushing 5. This tube 7 can be shrunk onto the bushing 5 and/or can be adhered to it there. The tube 7 permits equalizing motion of the rigid implant relative to the tissue surrounding it. A layer of metallic wool 8 is adhered to the flexible tube 7. The metallic wool acts as a germ barrier after the surrounding tissue has grown into it.

Distally, the flexible tube 7 transitions in one piece to a flexible screen network 19 with a large number of perforations 20, which after the operation, over the course of time, are infiltrated by muscle tissue.

Further, distally to the screen network 19, metallic wool 21 is adhered, which acts as a further germ barrier after the tissue material has grown into it.

Figure 3:
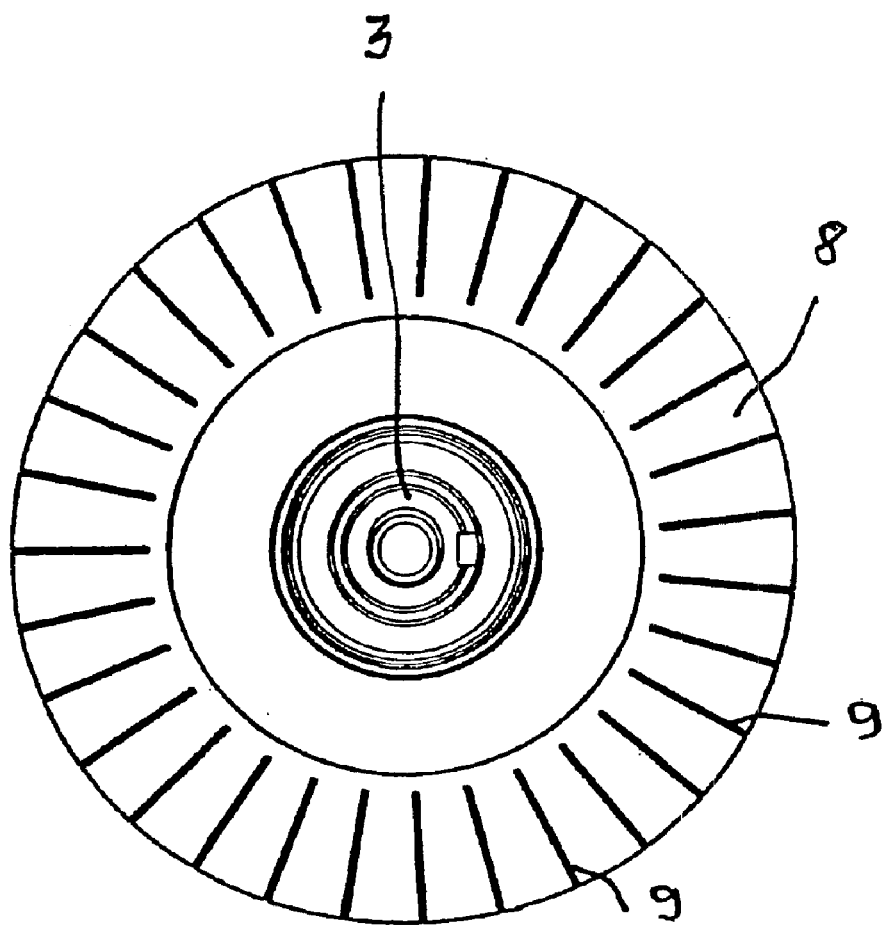
FIG. 3 is a distal view of the cap-shaped skirt according to FIG. 2.
Figure 2:
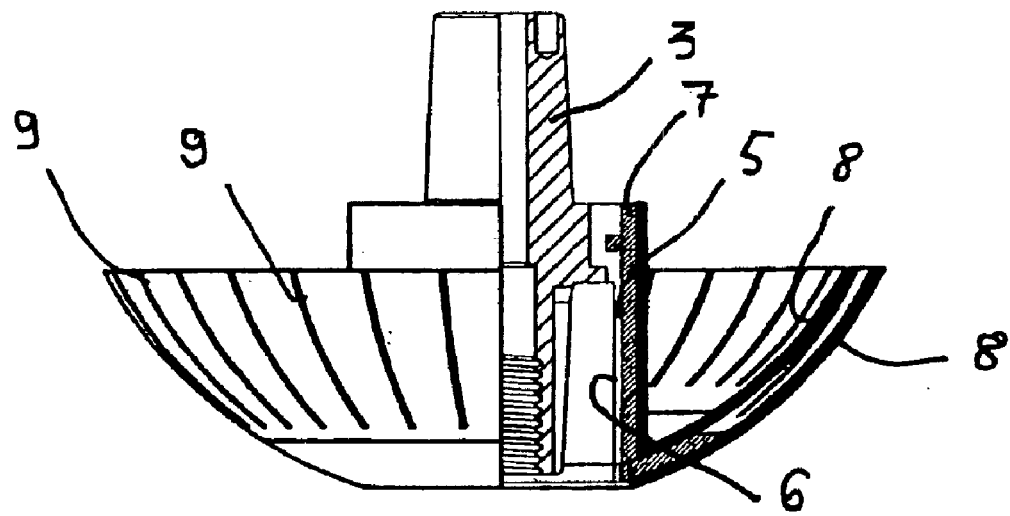
FIG. 2 is a schematic view, partially in a section, of the intermediate piece of the support with the cap-shaped skirt and through the multiple layers of the metallic web, fabric, mesh and/or the metallic wool, according to a preferred embodiment of the invention.

In the preferred embodiment according to FIGS. 2 and 3, a rigid bushing 5 is again firmly connected with the intermediate piece 3. The arrangement is likewise designed so that between the wall of the bushing 5 and the intermediate piece 3, there is formed an annulus 6 closed in the intracorporeal direction, into which the extracorporeal coupling device is inserted.

Applied on the outer wall of the bushing 5 is the tube 7 made of flexible material. This flexible tube 7 extends distally so that it surrounds the bushing 5 in the form of a cap. The flexible material of the tube 7 gives the arrangement its desired isoelasticity.

The tube 7 is covered on the outside by a layer of a multi-layered metallic web, fabric, mesh and/or a multi-layered metallic wool. Another layer of a multi-layered metallic web, fabric, mesh and/or the multi-layered metallic wool 8 is arranged distally, so that a layer of the porous material lies on each side of the bent over (turned inside out) end of the tube 7. Thus, tissue material can diffuse in from both sides, so that the multi-layered metallic web, fabric, mesh and/or the multi-layered metallic wool forms a secure germ barrier.

So that the multiple layers of metallic web, fabric, mesh and/or metallic wool can flexibly adapt to the anatomical circumstances, radially running lines 9 are provided here, along which the multiple layers of the metallic web, fabric, mesh and/or the metallic wool are fused together. If the lines 9 serve as cutting patterns, welding them together prevents fraying of the multi-layered metallic web, fabric, mesh and/or of the multi-layered metallic wool from occurring.

FIG. 3 shows the view from the distal end and again illustrates the arrangement of lines 9.

Figure 4:
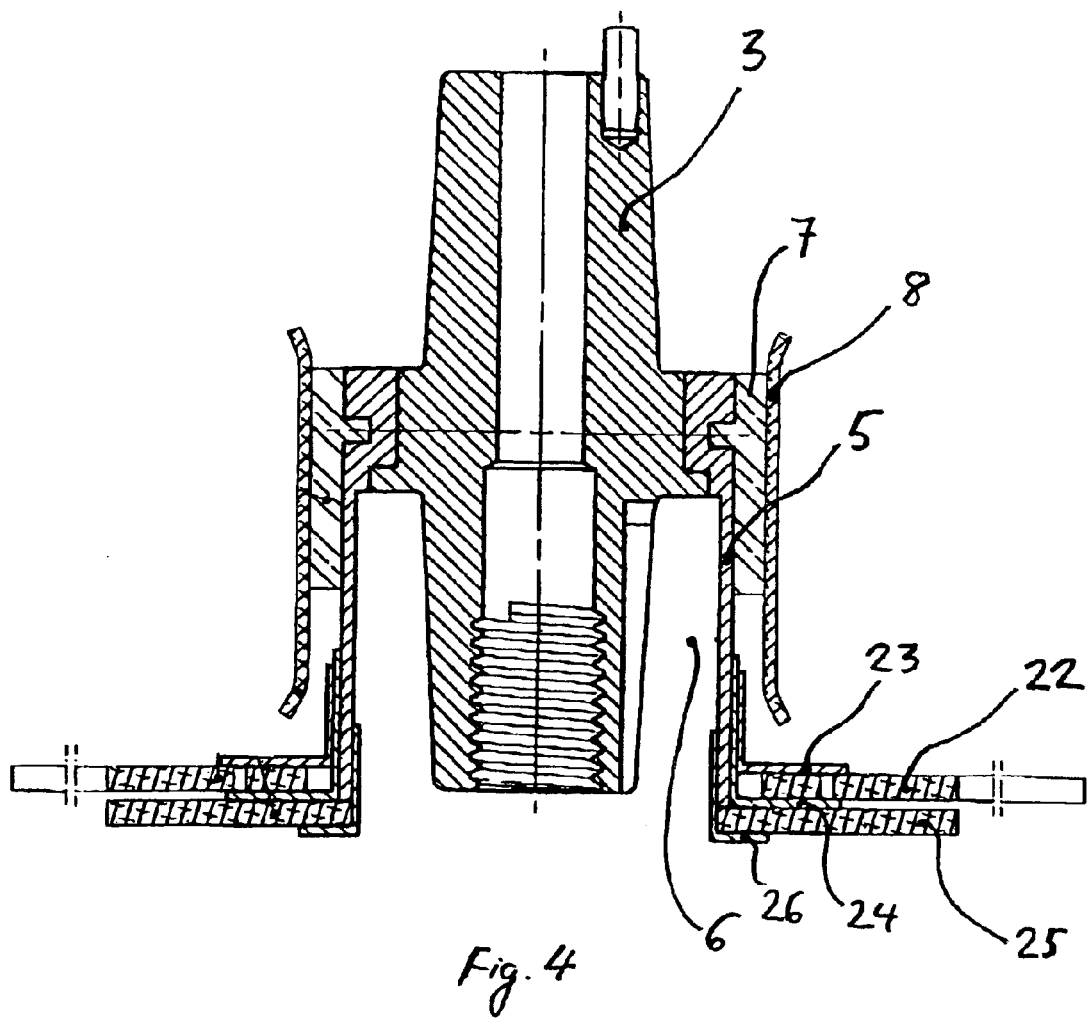
FIG. 4 is a schematic sectional view of the intermediate piece of the support in a further embodiment of the invention.

Another embodiment is shown in FIG. 4. Here, the flexible tube 7 sitting on the bushing 5 and the metallic wool 8 applied thereto are decoupled completely from the distal layers provided to form a germ barrier. In this embodiment, two slotted clamping rings 23 and 24 are pushed onto the bushing 5. These clamping rings are bent such that one leg runs parallel to the wall of the bushing 5 and the other leg projects away from the bushing. This allows the partial enclosure of a first layer 22 of a metallic web, mesh and/or metallic wool, into which the surrounding tissue can grow after the operation and thus form a germ barrier.

In the embodiment illustrated in FIG. 4, there is yet another layer 25 of a metallic web, fabric, mesh and/or attached metallic wool arranged between the distal clamping ring 24 and a slotted and bent locking ring 26. The locking ring 26 has one leg that runs parallel to the inner wall of the bushing 5, while the other leg projects freely from the bushing. During the operation, the surgeon will slide the clamping rings 23 and 24 onto the bushing 5 so far, according to the local circumstances, that a substantially stress-free position of the implant can be expected in the tissue that later surrounds the implant. When this position is found, it is locked into place by inserting one leg of the locking ring 26 into the annulus.

Layers 22 and 25 can preferably be constructed similar to the metallic wool 8 in the embodiment explained above and as shown in FIGS. 2 and 3.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A subcutaneous, intramuscular support (1) for a rigid transcutaneous implant (2) to be intracorporeally anchored in a bone stump, comprising:
   an intermediate piece (3) to be mounted between a part of the implant (2) to be intracorporeally anchored and an extracorporeal coupling device (4) couplable thereto;
   a rigid bushing (5) firmly connected with the intermediate piece (3), such that an annulus (6) is formed between a wall of the bushing (5) and the intermediate piece (3), the annulus being closed in an intracorporeal direction, and the extracorporeal coupling device (4) being insertable into the annulus;
   a tube (7) comprising flexible material applied to an outer wall of the bushing (5); and
   a metallic wool (8) applied to the tube (7).

2. The support according to claim 1, wherein the bushing (5) is firmly connected to the intermediate piece (3) by shrinking the bushing onto the intermediate piece.

3. The support according to claim 1, wherein the bushing (5) is welded to the intermediate piece (3).

4. The support according to claim 1, wherein the bushing (5) is constructed in one piece with the intermediate piece (3).

5. The support according to claim 1, wherein the tube (7) comprises silicone.

6. The support according to claim 1, wherein the metallic wool (8) comprises titanium fibers.

7. The support according to claim 1, wherein the intermediate piece (3) is a double cone with a cylindrical center section (9), and the bushing (5) is connected to the center section.

8. The support according to claim 1, wherein on the tube (7), a multi-layered metallic web, fabric, mesh and/or a multi-layered metallic wool (8) is applied, which extends around the intermediate piece (3) in a form of a cap.

9. The support according to claim 8, wherein the tube (7) extends from the bushing (5) in a form of a cap.

10. The support according to claim 9, wherein the tube (7) is covered on both sides by a multi-layered metallic web, fabric, mesh and/or a multi-layered metallic wool (8).

11. The support according to claim 8, wherein the multi-layered metallic web, fabric, mesh and/or the multi-layered metallic wool (8) has radially running lines (9) along which the multiple layers are welded together.

12. The support according to claim 1, further comprising at least two slotted, bent clamping rings (23, 24), which during an operation can be slid longitudinally onto the bushing (5) with little play, such that the at least two clamping rings partially grasp between a pair of adjacent rings one layer (22, 25) of a metallic web, fabric, mesh and/or attached metallic wool, wherein the layer extends around the intermediate piece (3) in a form of a cap.

13. The support according to claim 12, comprising more than two clamping rings (23, 24), wherein a layer is arranged between each pair of adjacent clamping rings.

14. The support according to claim 12, further comprising a slotted, bent locking ring (26), wherein the locking ring fits against an inner wall of the annulus (6) with very little play and locks the layer (25) most outwardly situated against the clamping ring (24) most outwardly situated.

* * * * *